United States Patent
Rousseau et al.

(10) Patent No.: US 11,806,410 B2
(45) Date of Patent: Nov. 7, 2023

(54) VEGETABLE PAPER COMPRISING BAST FIBRES AND COSMETIC PRODUCTS MADE THEREOF

(71) Applicant: Schweitzer-Mauduit International, Inc., Alpharetta, GA (US)

(72) Inventors: Cédric Rousseau, Spay (FR); Arthur Gouth, Spay (FR)

(73) Assignee: Mativ Holdings, Inc., Alpharetta, GA (US)

( * ) Notice: Subject to any disclaimer, the term of this patent is extended or adjusted under 35 U.S.C. 154(b) by 0 days.

(21) Appl. No.: 17/256,517

(22) PCT Filed: Jul. 3, 2019

(86) PCT No.: PCT/EP2019/067886
§ 371 (c)(1),
(2) Date: Dec. 28, 2020

(87) PCT Pub. No.: WO2020/007930
PCT Pub. Date: Jan. 9, 2020

(65) Prior Publication Data
US 2021/0220229 A1    Jul. 22, 2021

(30) Foreign Application Priority Data
Jul. 3, 2018   (FR) ..................... 18 56140

(51) Int. Cl.
| | | |
|---|---|---|
| *A61K 8/02* | (2006.01) | |
| *A61K 8/9767* | (2017.01) | |
| *A61K 8/9789* | (2017.01) | |
| *A61K 8/34* | (2006.01) | |
| *A61K 8/49* | (2006.01) | |
| *A61K 8/73* | (2006.01) | |
| *D21H 27/00* | (2006.01) | |

(52) U.S. Cl.
CPC ............ *A61K 8/0208* (2013.01); *A61K 8/347* (2013.01); *A61K 8/498* (2013.01); *A61K 8/731* (2013.01); *A61K 8/9767* (2017.08); *A61K 8/9789* (2017.08); *D21H 27/002* (2013.01); *A61K 2800/805* (2013.01)

(58) Field of Classification Search
CPC .... A61K 10/16; A61K 8/0208; A61K 8/9767; A61K 8/347; A61K 8/731; A61K 8/9789; A61K 8/0212; A61K 8/498; A61K 2800/805; D21H 11/12; D21H 27/002; A61Q 19/00
See application file for complete search history.

(56) References Cited

U.S. PATENT DOCUMENTS

| | | | |
|---|---|---|---|
| 10,844,538 B2 * | 11/2020 | Lee | ...................... D21H 17/675 |
| 2003/0099821 A1 | 5/2003 | Takai et al. | |
| 2015/0337496 A1 | 11/2015 | Lee | |
| 2019/0390408 A1 * | 12/2019 | Luxenbourg | ........... D21H 21/14 |

FOREIGN PATENT DOCUMENTS

| | | | |
|---|---|---|---|
| EP | 0745336 | * | 12/1996 |
| WO | WO 2009/133976 | * | 11/2009 |
| WO | WO 2013/044347 | | 4/2013 |
| WO | WO 2015179380 | * | 11/2015 |
| WO | WO 2017/174661 | | 10/2017 |

OTHER PUBLICATIONS

International Search Report for PCT/EP2019/067886 dated Jul. 17, 2019, 3 pages.
"2016-2017 Development Report of Disciplines of Textile Science and Technology", Chinese Science and Technology Press, Mar. 2018, pp. 134-135.

* cited by examiner

*Primary Examiner* — Lezah Roberts
(74) *Attorney, Agent, or Firm* — Dority & Manning, P.A.

(57) ABSTRACT

The invention relates to a vegetable paper comprising bast fibres, characterized in that the amount of bast fibres is at least 40% by weight of dry matter of the vegetable paper, and the bast fibres have a length-weighted average length of from 1 mm to 12 mm, and cosmetic products comprising the vegetable paper.

20 Claims, 3 Drawing Sheets

|  | 1-1 | 1-2 | 1-3 | 1-4 | 1-5 | 2-1 | 2-2 | 2-3 |
|---|---|---|---|---|---|---|---|---|
| Specific volume (dm³/kg) | 5.02 | 4.70 | 4.57 | 4.61 | 4.62 | 4.93 | 4.78 | 4.88 |

VEGETABLE PAPER COMPRISING BAST FIBRES AND COSMETIC PRODUCTS MADE THEREOF

RELATED APPLICATIONS

This application is the U.S. National Stage entry of International Application Number PCT/EP2019/067886 filed under the Patent Cooperation Treaty and having a filing date of Jul. 3, 2019, and which claims priority to French Application No. 1856140, filed on Jul. 3, 2018, both of which are hereby incorporated by reference in their entirety.

The invention relates to a vegetable paper comprising bast fibres, this vegetable paper being able to be used as a cosmetic product or a substrate for cosmetic product.

Cosmetic products are commonly used to moisturize the skin, to procure a radiant complexion, to purify the face or to firm the skin. Typically, the user applies the cosmetic products such as a face mask to her face for between 10 minutes and 20 minutes, the lotion it contains is then released onto her face to obtain the desired cosmetic effect. The success of cosmetic products is such that the worldwide demand has very greatly increased in recent years.

Cosmetic products such as cosmetics masks are mainly made of paper or of synthetic fibres. However, the processes for producing paper and synthetic fibres are very energy consuming and have a substantial ecological impact. Indeed, paper production consumes a great deal of wood derived from forests and requires the use of hazardous chemical products such as sodium hydroxide, chlorine, chlorine dioxide, oxygen, ozone or hydrogen peroxide. Synthetic fibres are, for their part, obtained by chemical synthesis and originate almost exclusively from hydrocarbons.

In order to limit the ecological impact of the production of cosmetic masks and also to propose more natural products, one solution consists in replacing the paper or the synthetic fibres with vegetable fibres, while at the same time ensuring that the face masks made of vegetable fibres meet users' needs.

A cosmetic mask must fulfil several characteristics to satisfy users. It must have a good sensory effect throughout its use, in particular it must be pleasant looking (shiny, natural) and pleasant on the skin (soft, silky, supple). It must also be pleasant to handle (easy to unfold and to lay, and not lose any particles). The cosmetic face mask must also have a good reservoir effect, i.e. it must be able to absorb cosmetic lotion which contains the cosmetic active agents in order to be able to deliver it to the skin. Furthermore, the cosmetic mask must also have moisture resistance properties to be resistant once it has been moistened/impregnated with lotion.

In one aspect of the invention, the inventors have developed a vegetable paper which can be used as a cosmetic product or as a substrate for cosmetic products.

Thus, the present invention relates to a vegetable paper comprising bast fibres, characterized in that the amount of bast fibres is at least 40% by weight of dry matter of said vegetable paper, and the length-weighted average length of the bast fibres is from 1 mm to 12 mm.

Advantageously, the vegetable paper according to the invention has a neutral odour, and a light and homogeneous colour. The vegetable paper according to the invention is also soft, light and supple. The vegetable paper according to the invention is easy to handle, in particular to unfold, and does not lose any particles. The vegetable paper according to the invention is also capable of absorbing and of releasing a cosmetic lotion satisfactorily. Furthermore, the vegetable paper according to the invention may be readily manufactured. By virtue of these properties, the vegetable paper according to the invention may be used as a substrate for cosmetic face masks.

For the purposes of the present patent application, the term "bast fibre" refers to a vegetable fibre contained in the phloem of plants.

Typically, the bast fibres are chosen from hemp fibre, Indian hemp fibre, jute fibre, kenaf fibre, kudzu fibre, *Dalbergia ecastaphyllum* fibre, flax fibre, okra fibre, nettle fibre, papyrus fibre, ramie fibre, sisal fibre, esparto fibre, and mixtures thereof, in particular from hemp fibre, flax fibre, and mixtures thereof, most particularly flax fibre.

According to one embodiment, the amount of bast fibres in the vegetable paper according to the invention is from 45% to 75%, in particular from 50% to 60% by weight of dry matter of said vegetable paper.

Typically, the bast fibres have a length-weighted average length of from 1.5 mm to 4 mm, most particularly from 1.95 mm to 2.05 mm.

According to a particular embodiment, the bast fibres have a length-weighted average length of from 3 mm to 6 mm, most particularly from 4 mm to 5 mm.

According to another particular embodiment, the bast fibres have a length-weighted average length of from 7 mm to 11.5 mm, most particularly from 9 mm to 11 mm.

The length of the fibres is measured with a MorFI LABO (LB-01) machine from TECHPAP. Bast fibres are placed in water to a concentration of 300 mg/L and then 30 mg/L. The camera of the MorFI LABO (LB-01) machine measures the developed length (Li) of each of the bast fibres present in the field of vision of said camera.

The length-weighted average length, Lwl, is calculated using the following formulae:

$$Lwl = \frac{\sum Li \times Li}{\sum Li}.$$

Typically, the bast fibres are chopped so that the length-weighted average length of the bast fibres is within the ranges mentioned above. Typically, the chopping techniques are those known to a person skilled in the art, such as guillotine chopping.

Conventionally, the bast fibres are produced from bast stems, via scutching and combing processes which are aimed at separating the fibres from the ligneous part which are in the form of small particles known as straws. For example, these straws are known as shives for flax fibres and are known as chaff for hemp fibres.

Typically, the residual content of straw in the bast fibres of the vegetable paper according to the invention is less than 2% by weight relative to the weight of bast fibres, in particular less than 1% by weight relative to the weight of bast fibres, and even more particularly less than 0.5% by weight in comparison with the weight of bast fibres.

The content of straw is determined in the following manner. The straw is harvested manually in a sample of 100 g of bast fibres composition, and then weighed to calculate the mass ratio.

Typically, the processes of scutching and combing of the bast fibres make it possible to remove the straw and to achieve the desired content of straws.

The straw is not aesthetically pleasing. Furthermore, if the content of straw is greater than the ranges mentioned above, then the vegetable paper according to the invention is abrasive.

Typically, the bast fibres may have undergone extraction in a solvent. This extraction makes it possible to extract the compounds of the bast fibre that are soluble in the solvent (referred to hereinbelow as the soluble compounds).

The mixture of these soluble compounds and of the solvent is generally of a dark colour and may be odorous. Advantageously, the vegetable paper comprising bast fibres which have undergone extraction in a solvent has a neutral smell and a light colour.

The extraction in the solvent performed to extract the soluble compounds is a mild method which does not involve compounds such as sodium hydroxide. It is also different from the delignification treatments commonly used in papermaking for the production of paper pulp and from bleaching treatments. Typically, the delignification treatments commonly used in papermaking are those known as mechanical pulp, thermomechanical pulp, chemomechanical pulp or chemical pulp. Typically, the bleaching treatments are those using chlorine, chlorine dioxide, oxygen, ozone or hydrogen peroxide. Advantageously, the ecological impact of the extraction in a solvent is less than that of the delignification and bleaching treatments mentioned above. Consequently, the ecological impact of the vegetable paper comprising bast fibres which have undergone extraction in a solvent is less than the ecological impact of paper.

According to a particular embodiment, the solvent is an aqueous solvent; most particularly, the solvent is water.

Typically, the aqueous solvent may be a 70-30 (v/v) water/alcohol mixture.

According to the embodiment in which the solvent is water, the extraction is performed at atmospheric pressure and the temperature of the water is from 40° C. to 100° C., in particular from 60° C. to 90° C.

Typically, the bast fibres which have undergone extraction in a solvent are obtained after extraction in the solvent and separation from the soluble compounds. The bast fibres which have undergone extraction in a solvent may thus comprise a residual fraction of soluble compounds. Typically, the vegetable paper comprising bast fibres which have undergone extraction in a solvent may thus comprise less than 10% of soluble compounds by weight of dry matter of said vegetable paper. Typically, the vegetable paper comprising bast fibres which have undergone extraction in a solvent may comprise less than 5%, less than 4%, less than 3%, less than 2%, less than 1% of soluble compounds by weight of dry matter of said vegetable paper. According to a particular embodiment, the vegetable paper comprising bast fibres which have undergone extraction in a solvent does not comprise any soluble compounds.

Use will be made of the following technique to determine the percentage of soluble compounds by weight of dry matter of said vegetable paper. The vegetable paper to be analysed is ground so as to achieve a particle size of less than or equal to 2 mm. The ground vegetable paper is then mixed with boiling water for 10 minutes so as to extract the soluble compounds. The weight of dry matter in the vegetable paper of compounds of the bast fibres that are soluble in the solvent is calculated by the difference between the dry weight of the vegetable paper sample and the dry weight of the fibrous residue after extraction.

The vegetable paper according to the invention may also comprise cellulose fibres.

Typically, the cellulose fibres may be chosen from traditional cellulose fibres originating from wood pulps (delignified and bleached, or otherwise) derived from softwood or hardwood and from a mixture of softwood and hardwood, and/or artificial cellulose fibres such as lyocell fibres, viscose fibres, cellulose acetate fibres, and mixtures thereof.

According to one embodiment, the vegetable paper comprises cellulose fibres chosen from wood pulp, lyocell fibres, viscose fibres, cellulose acetate fibres, and mixtures thereof.

Typically, the amount of cellulose fibres in the vegetable paper according to the invention is from 20% to 60% by weight of dry matter of said vegetable paper, in particular from 40% to 50% by weight of dry matter of said vegetable paper.

Typically, the amount of lyocell fibres in the vegetable paper according to the invention is from 10% to 40% by weight of dry matter of said vegetable paper, in particular from 15% to 35% by weight of dry matter of said vegetable paper.

Typically, the lyocell fibres in the vegetable paper have a length-weighted average length of from 1 mm to 58 mm, in particular from 4 mm to 20 mm, and most particularly from 5.5 mm to 6.5 mm.

Typically, the lyocell fibres in the vegetable paper have a fineness of from 0.5 dTex to 2.5 dTex, in particular from 1 dTex to 2 dTex, and most particularly from 1.65 dTex to 1.75 dTex.

Typically, the viscose fibres in the vegetable paper have a length-weighted average length of from 1 mm to 58 mm, in particular from 4 mm to 20 mm, and most particularly from 5.5 mm to 6.5 mm.

Typically, the viscose fibres in the vegetable paper have a fineness of from 0.5 dTex to 2.5 dTex, in particular from 1 dTex to 2 dTex, most particularly from 1.65 dTex to 1.75 dTex.

Typically, the amount of viscose fibres in the vegetable paper according to the invention is from 10% to 40% by weight of dry matter of said vegetable paper, in particular from 15% to 35% by weight of dry matter of said vegetable paper.

Typically, the cellulose acetate fibres in the vegetable paper have a length-weighted average length of from 1 mm to 58 mm, in particular from 4 mm to 20 mm, and most particularly from 5.5 mm to 6.5 mm.

Typically, the cellulose acetate fibres in the vegetable paper have a fineness of from 0.5 dTex to 2.5 dTex, in particular from 1 dTex to 2 dTex, and most particularly from 1.65 dTex to 1.75 dTex.

Typically, the amount of cellulose acetate fibres in the vegetable paper according to the invention is from 10% to 40% by weight of dry matter of said vegetable paper, in particular from 15% to 35% by weight of dry matter of said vegetable paper.

Typically, the amount of cellulose fibres originating from wood pulp in the vegetable paper according to the invention is from 10% to 40% by weight of dry matter of the vegetable paper, in particular from 15% to 35% by weight of dry matter of the vegetable paper.

Typically, the cellulose fibres originating from wood pulp are refined and have a degree Schopper-Riegler (° SR) of from 15° SR to 90° SR, in particular from 30° SR to 75° SR, and most particularly from 50° SR to 65° SR.

Typically, the wood pulp is a hardwood pulp, a softwood pulp, and mixtures thereof.

According to a particular embodiment, the wood pulp is a softwood pulp.

The cellulose fibres may be added to the vegetable paper in order to modify the properties of said vegetable paper. Typically, the properties of the vegetable paper that may be modified are the mechanical strength properties such as the dry and wet tensile strength, the tear strength, the bursting strength, the folding resistance, the flexural strength, the sensory properties such as the softness to the touch, the optical properties such as the whiteness, the opacity or the gloss, or other properties such as the basis weight, the porosity, the permeability to air or to a liquid, the specific volume ("la main" in French), the absorption capacities and the release capacities.

Advantageously, the lyocell fibres described above increase the softness and the dry strength of the vegetable paper according to the invention, and the wood pulps described above increase the mechanical strength properties and the absorption capacity of the vegetable paper according to the invention.

The vegetable paper may also comprise an additive usually used for paper manufacture so as to develop or to give the vegetable paper new properties, for instance chemical, optical, sensory or mechanical properties such as dry strength, wet strength and/or folding resistance.

Typically, the additive may be chosen from a wet strength agent, a dry strength agent, a softening agent, a lotion composition, a wetting agent, latex, a cannabinoid such as cannabidiol (CBD) and tetrahydrocannabinol (THC), and mixtures thereof, in particular chosen from a wet strength agent, a dry strength agent, a lotion composition, a cannabinoid such as cannabidiol (CBD) and tetrahydrocannabinol (THC), and mixtures thereof, and most particularly a wet strength agent.

According to one embodiment of the invention, the additive may be a cannabinoid such as cannabidiol (CBD) or tetrahydrocannabinol (THC), in particular cannabidiol (CBD).

Typically, the amount of additive is less than 3% by weight of dry matter of the vegetable paper, in particular from 0.5% to 2% by weight of dry matter of the vegetable paper, and most particularly from 1.3% to 1.7% by weight of dry matter of the vegetable paper.

A wet strength agent makes it possible to reduce the potential degradation of the vegetable paper if the latter is placed in contact with a liquid, such as water. Typically, the wet strength agent may be chosen from polyamides, such as an epichlorohydrin resin, a polyamine-epichlorohydrin resin, a polyamide-epichlorohydrin resin, a poly(aminoamide)-epichlorohydrin resin, a urea-formaldehyde resin, a melamine-formaldehyde resin, an alkyl-ketene dimer, alkylsuccinic anhydride, a polyvinylamine, an oxidized polysaccharide, and mixtures thereof.

A dry strength agent makes it possible to increase the strength of the vegetable paper if the latter is subjected to substantial mechanical stresses. The dry strength agent may be chosen from starches and modified gums, cellulose polymers, synthetic polymers, for instance carboxymethylcellulose, polyacrylamides, and mixtures thereof.

A softening agent makes it possible to improve the softness of the vegetable paper according to the invention. Typically, a softening agent is a fatty acid, a siloxane compound, a silicone compound, an amino silicone compound, an Aloe vera extract, a sweet almond extract, a chamomile extract, a quaternary ammonium compound, and mixtures thereof.

Typically, the vegetable paper according to the invention has a basis weight of from 15 g/m² to 70 g/m², in particular from 35 g/m² to 60 g/m².

Advantageously, a basis weight within these ranges of values gives the vegetable paper according to the invention its conformability (ability of the vegetable paper according to the invention to take the form of a user's face) and an absorption capacity and a release capacity that are satisfactory for cosmetic use.

Typically, when the vegetable paper according to the invention comprises bast fibres and cellulose fibres, in particular a mixture of lyocell fibres and of softwood pulp, the mixture of bast fibres and of cellulose fibres may have a degree Schopper-Riegler (° SR) of from 5° SR to 50° SR, in particular from 10° SR to 25° SR, and most particularly from 11° SR to 14° SR.

Advantageously, a degree Schopper-Riegler within these ranges of values gives the vegetable paper according to the invention mechanical strength properties such that said vegetable paper may be used even if it is wet and such that it may be readily shaped.

According to a specific embodiment, the vegetable paper according to the invention comprises:
  flax fibres which have undergone extraction and which have a length-weighted average length of from 1.95 mm to 2.05 mm,
  lyocell fibres with a length-weighted average length of from 5.5 mm to 6.5 mm and a fineness of from 1.65 dTex to 1.75 dTex,
  a softwood pulp with a degree Schopper-Riegler (° SR) of from 60° SR to 65° SR, and
  a wet strength agent,
  in which
  the amount of said flax fibres is from 45% to 55% by weight of dry matter of said vegetable paper,
  the amount of said lyocell fibres is from 20% to 30% by weight of dry matter of said vegetable paper,
  the amount of said softwood pulp is from 20% to 30% by weight of dry matter of said vegetable paper, and
  the amount of wet strength agent is from 1.4% to 1.6% by weight of dry matter of said vegetable paper.

According to another specific embodiment, the vegetable paper according to the invention comprises:
  flax fibres which have undergone extraction and which have a length-weighted average length of from 1.95 mm to 2.05 mm,
  lyocell fibres with a length-weighted average length of from 5.5 mm to 6.5 mm and a fineness of from 1.65 dTex to 1.75 dTex,
  a softwood pulp with a degree Schopper-Riegler (° SR) of from 50° SR to 55° SR, and
  a wet strength agent,
  in which
  the amount of said flax fibres is from 45% to 55% by weight of dry matter of said vegetable paper,
  the amount of said lyocell fibres is from 20% to 30% by weight of dry matter of said vegetable paper,
  the amount of said softwood pulp is from 20% to 30% by weight of dry matter of said vegetable paper, and
  the amount of wet strength agent is from 1.4% to 1.6% by weight of dry matter of said vegetable paper.

According to another embodiment, the vegetable paper according to the invention comprises:
  hemp fibres which have undergone extraction and which have a length-weighted average length of from 1.95 mm to 2.05 mm,
  lyocell fibres with a length-weighted average length of from 5.5 mm to 6.5 mm and a fineness of from 1.65 dTex to 1.75 dTex,
  a softwood pulp with a degree Schopper-Riegler (° SR) of from 50° SR to 55° SR, and
  a wet strength agent, in which the amount of said hemp fibres is from 45% to 55% by weight of dry matter of said vegetable paper, the amount of said lyocell fibres is from 20% to 30% by weight of dry matter of said vegetable paper, the amount of said softwood pulp is from 20% to 30% by weight of dry matter of said vegetable paper, and the amount of wet strength agent is from 1.4% to 1.6% by weight of dry matter of said vegetable paper.

The vegetable paper according to the invention may also be used with a second paper to form a hybrid paper.

This second paper may be manufactured via processes known to those skilled in the art, such as the wet laid process, the drylaid carded process using long artificial fibres, long natural fibres, cellulose fibres, and mixtures thereof, or the airlaid process using long artificial fibres, long natural fibres, cellulose fibres, and mixtures thereof. This second paper may also be a spunbound support.

The cellulose fibres of the second paper may be as described above in relation with the vegetable paper.

According to one embodiment of the invention, the hybrid paper may comprise the vegetable paper according to the invention and the second paper; in particular, the vegetable paper is complexed with the second paper.

Typically, the hybrid paper may be obtained via a hydroentanglement process using the vegetable paper according to the invention, as first layer, and the second paper, as second layer.

According to one embodiment, the invention also relates to a process for manufacturing a hybrid paper in which the vegetable paper according to the invention is complexed with a second paper by hydroentanglement.

According to this embodiment, the second paper is as described above in relation with the hybrid paper.

By virtue of its sensory properties, its absorption and its release capacities, the vegetable paper and the hybrid paper may be or may be used as a substrate for a cosmetic product, a wipe, a hygiene product and an absorbent paper.

Typically, the cosmetic product may be a face mask, an eye patch, a body envelope or a wipe.

Typically, the cosmetic product according to the invention may comprise, in addition to the vegetable paper or the hybrid paper according to the invention, an active principle chosen from sebum regulators, antimicrobial agents, antibacterial agents, matt-effect agents, astringents, acidifying agents, cicatrizing agents, exfoliants, kerato-regulating agents, occlusive agents, protective agents, disinfectants, emollients, nourishing agents, moisturizers, anti-ageing agents, calmatives, decongestants or veinotonic agents, occlusive agents, UV-screening agents, humectants, hygroscopic agents, gelling agents, exfoliants, anti-free radical, cell-regenerating or cell-stimulating agents, firming agents, tautening agents, anti-glycation agents, lightening agents, and mixtures thereof.

Typically, the wipe according to the invention may comprise, in addition to the vegetable paper or the hybrid paper according to the invention, a softening agent such as a fatty acid, a siloxane compound, a silicone compound, an amino silicone compound, an Aloe vera extract, a sweet almond extract, a chamomile extract, a quaternary ammonium compound, a biocidal compound such as a disinfectant, an antimicrobial agent, an antibacterial agent, and mixtures thereof, a decongestant agent such as an extract of menthol or of eucalyptus, a fragrance, a moisturizing compound such as vitamin E, and mixtures thereof.

According to one embodiment, a hygiene paper according to the invention may comprise the vegetable paper or the hybrid paper.

According to one embodiment, an absorbent paper according to the invention may comprise the vegetable paper or the hybrid paper.

Typically, the vegetable paper according to the invention may be manufactured via a wet process, in particular via a wet process involving an inclined ascending dewatering fabric (commonly referred to in paper-making as an "inclined wire").

Typically, according to the wet process involving a dewatering fabric, the bast fibres are mixed with water to form a pulp. This pulp is then sent onto the dewatering fabric, allowing the formation of a web and then dewatering of the water on suction boxes.

A person skilled in the art will know how to adapt the parameters of the wet process involving a dewatering fabric to manufacture the vegetable paper according to the invention.

The fibres of the vegetable paper according to the invention agglomerate little or not at all in the wet manufacturing process. Conventionally, fibre agglomerates may give rise to problems of implementation of the wet manufacturing process. Advantageously, the vegetable paper according to the invention may thus be readily manufactured via the wet manufacturing process.

The bast fibres of the vegetable paper according to the invention may have undergone extraction in a solvent. In this case, the process for manufacturing the vegetable paper according to the invention comprises the following steps:
  a) mixing bast fibres with a solvent to extract all or some of the bast fibre compounds that are soluble in the solvent,
  b) separating the bast fibres from the soluble compounds to obtain bast fibres which have undergone extraction in a solvent,
  c) formation of the vegetable paper via a wet process using the bast fibres which have undergone extraction in a solvent.

In such a process, the bast fibres are mixed with the solvent, for example in an extractor, so as to extract the bast fibre compounds that are soluble in the solvent. These compounds that are soluble in the solvent are then separated from the bast fibres, for example by passing through a screw press, to obtain, on the one hand, the bast fibres which have undergone extraction in a solvent, and, on the other hand, the extract that is soluble in the solvent. The bast fibres which have undergone extraction in a solvent are then mixed with water to form the pulp which is sent onto the inclined ascending dewatering fabric (inclined wire) to form the vegetable paper according to the invention.

According to a particular embodiment, the solvent is an aqueous solvent; most particularly, the solvent is water.

According to the embodiment in which the solvent is water, the temperature of the water may be adapted to the bast fibres to be treated. Typically, the temperature of the water is from 40° C. to 100° C., in particular from 60° C. to 90° C.

If the vegetable paper also comprises cellulose fibres, then these fibres may be mixed with the bast fibres or with the bast fibre mixture to form a fibre mixture, and this fibre mixture is then mixed with water to form the pulp, this being the pulp that is sent onto the inclined ascending dewatering fabric (inclined wire) to form the vegetable paper according to the invention.

If the vegetable paper comprises an additive, in particular a wet strength agent, then this additive may be added to the bast fibres and, optionally, to the cellulose fibres, before they are mixed with water to form the pulp. The additive may also be added directly to the vegetable paper formed by using a size press, by coating or by spraying.

Typically, before being mixed with water, the fibre mixture may pass, for example, through a refiner to adjust the Schopper-Riegler degree of said fibre mixture from 10° SR to 50° SR, most particularly from 12° SR to 14° SR.

Once manufactured, the vegetable paper may be dried by a drying device, such as drying rollers.

The vegetable paper may then be shaped in the form of sheets or leaflets or rolled up as a roll which may then be cut into bobbins or bands.

The vegetable paper may also undergo additional treatments known in the papermaking industry.

Typically, one of these treatments allows the manufacture of a multilayer vegetable paper using multiple head boxes. Each layer may have the same or different compositions of fibres and/or additives.

Another of these additional treatments is hydroentanglement. This treatment uses high-pressure water jets to entangle the fibres. Gripped between a grate and a compression strip, the vegetable paper according to the invention is first compacted and moistened to prevent the formation of air pockets. Circulating on a perforated cylinder covered with a fine gauze, the vegetable paper according to the invention is subjected to high-pressure water jets on one face, and then on the other. Typically, the water jets are emitted by injectors, i.e. holes, typically from 80 μm to 150 μm in diameter, arranged at a rate of 1 to 3 holes per millimetre, on rows typically 3 mm to 5 mm apart. The water pressure increases from the first to the last injectors. To avoid inundating the vegetable paper according to the invention, the interior of the cylinders is under negative pressure. The residual water is removed first by suction, and then by drying.

Advantageously, the sensory properties, in particular the softness, and the absorption capacity of the vegetable paper which has undergone a hydroentanglement treatment are improved. Furthermore, the vegetable paper which has undergone a hydroentanglement treatment may form harmonious folds when it is suspended, it has greater tensile strength, and is easy to shape. Due to the improvement in its sensory properties, and in particular its softness and its conformability, the vegetable paper which has undergone the hydroentanglement treatment may also, and advantageously, may be, or be used as a substrate for, the cosmetic product, the wipe, the hygiene product and the absorbent paper described previously.

EXAMPLES

Example 1: Vegetable Paper with Flax Fibres

Example 1-1: Vegetable Paper with Flax Fibres, Tencel Fibres and Södra Blue, the Vegetable Paper Having a Basis Weight of 50 g/m² and the Fibre Mixture Having a Schopper-Riegler Degree of 12° SR A vegetable paper comprising 50% of flax fibres, 30% of glossy Tencel® lyocell fibres of 6 mm and 1.7 dTex available from Lenzing AG, 20% of Södra blue 85Z wood pulp refined to 53° SR available from Södra, and 1.5% of Kymene GHP20 BF (a wet strength agent) available from Solenis was manufactured. The percentages are expressed on a weight basis relative to the weight of the dry matter of the vegetable paper.

The flax fibres have a length-weighted average length of from 1.95 mm to 2.05 mm. The flax fibres were mixed with water at 70° C.±10° C. for 50 minutes. The mixture then undergoes a step of extraction in a screw press to separate the flax fibres from the aqueous part comprising the flax fibre compounds that are water-soluble.

The Södra blue 85Z was refined for 25 minutes in a 24" offline refiner with a power set point of 170 kW.

The flax fibres which have undergone the extraction in water are mixed with the Tencell® fibres and with the refined Södra blue to form a fibre mixture. This fibre mixture is then mixed with water to form a pulp. This pulp then passes onto an inclined wire paper-making machine to manufacture the vegetable paper.

Example 1-2: Vegetable Paper with Flax Fibres, Tencel Fibres and Södra Blue, the Vegetable Paper Having a Basis Weight of 50 g/m² and the Fibre Mixture Having a Schopper-Riegler Degree of 13° SR The vegetable paper of Example 1-2 is manufactured in a similar manner to the vegetable paper of Example 1-1. The only difference is that the fibre mixture is refined using a 14" online refiner with a power set point of 40 kW before passing onto the inclined wire paper-making machine to obtain the vegetable paper.

This refining step makes it possible to increase the Schopper-Riegler degree of the fibre mixture.

Example 1-3: Vegetable Paper with Flax Fibres, Tencel Fibres and Södra Blue, the Vegetable Paper Having a Basis Weight of 45 g/m² and the Fibre Mixture Having a Schopper-Riegler Degree of 13° SR The vegetable paper of Example 1-3 is manufactured in a similar manner to the vegetable paper of Example 1-2, the only difference being the basis weight of the vegetable paper of Example 1-3. A person skilled in the art knows how to adapt the wet-route paper manufacturing process to vary the basis weight of the vegetable paper.

Example 1-4: Vegetable Paper with Flax Fibres, Tencell Fibres and Södra Blue, the Vegetable Paper Having a Basis Weight of 50 g/m² and the Fibre Mixture Having a Schopper-Riegler Degree of 13° SR A vegetable paper comprising 50% of flax fibres of 2 mm, 20% of glossy Tencell® fibres of 6 mm and 1.7 dTex, 30% of Södra blue 85Z refined to 61° SR and 1.5% of Kymene GHP20 BF (a wet strength agent) was manufactured via a wet route. The percentages are expressed on a weight basis relative to the weight of the dry matter of the vegetable paper.

90% by number of the flax fibres have a length of from 1.95 mm to 2.05 mm. The flax fibres were mixed with water at 70° C.±10° C. for 45 minutes on average. The mixture then undergoes a step of extraction in a hydraulic press to separate the flax fibres from the aqueous part comprising the water-soluble flax fibre compounds.

The Södra blue 85Z was refined for 30 minutes in a 24" refiner with a power set point power of 170 kW.

The flax fibres which have undergone extraction in water are mixed with the Tencell® fibres, the refined Södra blue and water to form a pulp. This pulp then passes onto an inclined wire paper-making machine to obtain the vegetable paper.

Example 1-5: Vegetable Paper with Flax Fibres, Tencel Fibres and Södra Blue, the Vegetable Paper Having a Basis Weight of 45 g/m² and the Fibre Mixture Having a Schopper-Riegler Degree of 13° SR The vegetable paper of Example 1-5 is obtained in a similar manner to the vegetable paper of Example 1-4, the only difference being the basis weight of the vegetable paper of Example 1-5. A person skilled in the art knows how to adapt the wet-route paper manufacturing process to vary the basis weight of the vegetable paper.

The vegetable papers of Examples 1-1 to 1-5 are summarized in Table 1 below:

TABLE 1

|  | Example | | | | |
| --- | --- | --- | --- | --- | --- |
|  | 1-1 | 1-2 | 1-3 | 1-4 | 1-5 |
| Composition | 50% flax fibres, 30% glossy Tencel 6 mm 1.7 dTex, 20% of Södra Blue 85Z, 1.5% Kymene GHP20 BF | | | 50% flax fibres, 20% glossy Tencel 6 mm 1.7 dTex, 30% of Södra Blue 85Z, 1.5% Kymene GHP20 BF | |
| Basis weight | 50 g/m² | 50 g/m² | 45 g/m² | 50 g/m² | 45 g/m² |
| ° SR | | 53° SR | | 61° SR | |
| Södra Blue 85Z ° SR fibre mixture | 12° SR | 13° SR | 13° SR | 13° SR | 13° SR |

Example 2: Vegetable Paper with Hemp Fibres

Example 2-1: Vegetable Paper with Hemp Fibres, Tencell Fibres and Södra Blue, the Vegetable Paper Having a Basis Weight of 60 g/m²

A vegetable paper comprising 50% of hemp fibres of 2 mm, 30% of glossy Tencell® fibres of 6 mm and 1.7 dTex, 20% of Södra blue 85Z refined to 37° SR and 1.5% of Kymene GHP20 BF (a wet strength agent) was manufactured via a wet route. The percentages are expressed on a weight basis relative to the weight of the dry matter of the vegetable paper.

The hemp fibres have a length-weighted average length of from 1.95 mm to 2.05 mm. The hemp fibres were mixed with water at 85° C.±5° C. for 45 minutes. The mixture then undergoes a step of mechanical extraction to separate the hemp fibres from the aqueous part comprising the water-soluble hemp fibre compounds.

The hemp fibres which have undergone the extraction in water are mixed with the Tencel® fibres and the refined Södra blue 85Z to form a fibre mixture. This fibre mixture is then mixed with water to form a pulp. This pulp then passes onto an inclined wire paper-making machine to obtain the vegetable paper.

Example 2-2: Vegetable Paper with Hemp Fibres, Tencell Fibres and Södra Blue, the Vegetable Paper Having a Basis Weight of 50 g/m²

The vegetable paper of Example 2-2 is manufactured in a similar manner to the vegetable paper of Example 2-1. The only difference is that the fibre mixture is refined using a 14" refiner with a power set point of 55 kW before passing onto the inclined ascending dewatering fabric to obtain the vegetable paper. A person skilled in the art knows how to adapt the wet-route paper manufacturing process to vary the basis weight of the vegetable paper.

Example 2-3: Vegetable Paper with Hemp Fibres, Tencell Fibres and Södra Blue, the Vegetable Paper Having a Basis Weight of 50 g/m²

The vegetable paper of Example 2-3 is manufactured in a similar manner to the vegetable paper of Example 2-1. The only differences are the basis weight of the vegetable paper of Example 2-1 and that the fibre mixture is refined using a 14" refiner with a power set point of 45 kW before passing onto the inclined ascending dewatering fabric to obtain the vegetable paper. A person skilled in the art knows how to adapt the wet-route paper manufacturing process to vary the basis weight of the vegetable paper.

The vegetable papers of Examples 2-1 to 2-3 are summarized in Table 2 below:

TABLE 2

|  | Example | | |
| --- | --- | --- | --- |
|  | 2-1 | 2-2 | 2-3 |
| Composition | 50% hemp fibres, 30% glossy Tencel 6 mm 1.7 dTex, 20% of Södra Blue 85Z, 1.5% Kymene GHP20 BF | | |
| Basis weight | 50 g/m² | 50 g/m² | 45 g/m² |
| ° SR Södra Blue 85 Z | | 53° SR | |

Example 3: Properties of the Vegetable Papers of Examples 1 and 2

Example 3-1: Sensory Properties

The sensory properties of the vegetable papers of Examples 1 and 2 are evaluated by cosmetic panels which are organized with several panelists.

The vegetable papers of Example 1 have:
a very positive appearance since they have a light colour, are homogeneous and without straw,
a very positive tactile effect since they are soft and have a "light" and non-papery veil aspect,
satisfactory strength, in particular for the papers of Examples 1-2 and 1-5, and
ease of handling and of unfolding.

Furthermore, the vegetable papers with flax fibres of Example 1 do not lose any particles.

The vegetable papers with hemp fibres of Example 2 have:
a very positive appearance because they have a light and neutral colour and are glossy,
a very positive tactile effect because they are soft, and
a neutral odour.

The vegetable papers of Examples 1 and 2 have sensory properties such that they could be used as substrate for cosmetic face masks.

Example 3-2: Evaluation of the Reservoir Effect

Figure 1:
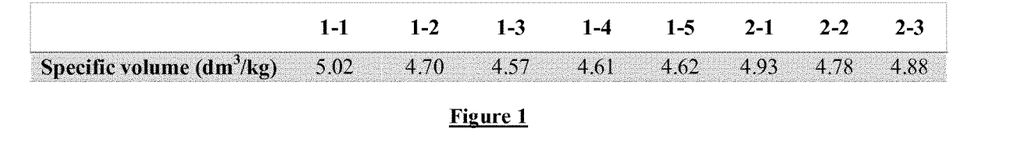

The reservoir effect is characterized by the specific volume (m³/kg). FIG. 1 illustrates the specific volume for the eight exemplified vegetable papers.

All the exemplified vegetable papers have a specific volume of greater than 4.55 dm³/kg. This is entirely satisfactory for use of the vegetable papers of Examples 1 and 2 as a cosmetic product or as a substrate for cosmetic masks.

Example 3-3: Evaluation of the Absorption and Release Capacities

The absorption and release capacities of each exemplified vegetable paper are measured as follows:
- a sheet of exemplified vegetable paper is weighed (m1) and folded into four,
- an aluminium plate is filled with 150 ml of water or of Technature cosmetic lotion (available from Tech Nature),
- the sheet of paper folded into four is placed in the plate and held under the water or Technature lotion for 2 minutes,
- the sheet is then removed from the plate and drained for 30 seconds,
- the drained sheet is then weighed (m2) to determine the absorption capacity (Ca) according to the formula Ca=(m2−m1)/m1*100,
- the sheet is then placed on an operator's arm and weighed each minute to determine the release capacity of the sheet (the sheet is returned to the arm after each weighing).

Figure 2:
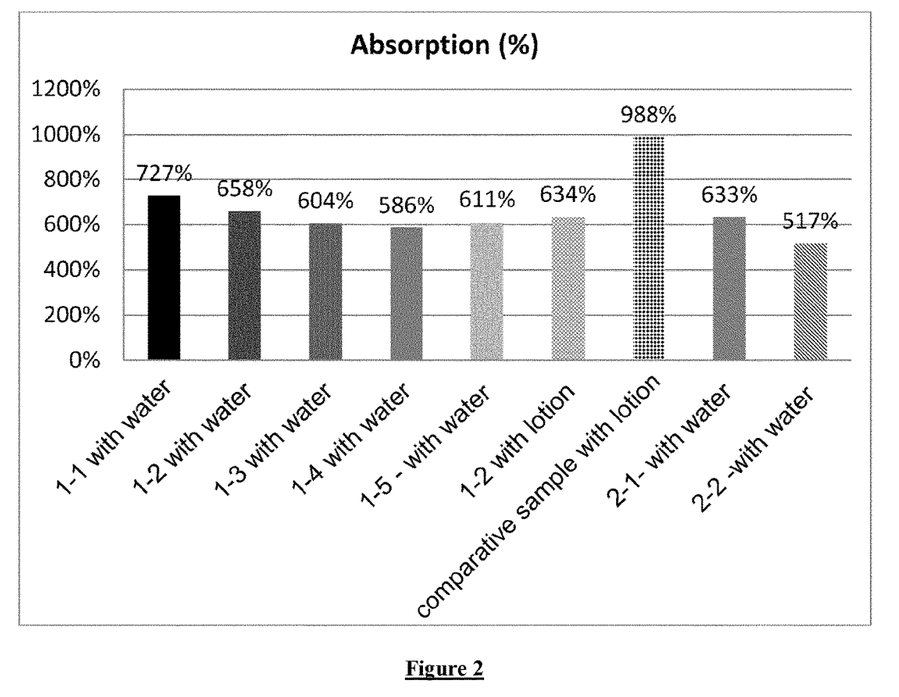

FIG. 2 illustrates the absorption capacity for the vegetable papers of Examples 1-1 to 2-2 with water, for the vegetable paper of Example 1-2 with the Technature lotion and for a commercial face mask made of synthetic fibres with the Technature lotion (referred as comparative sample with lotion in FIG. 2).

Figure 3:
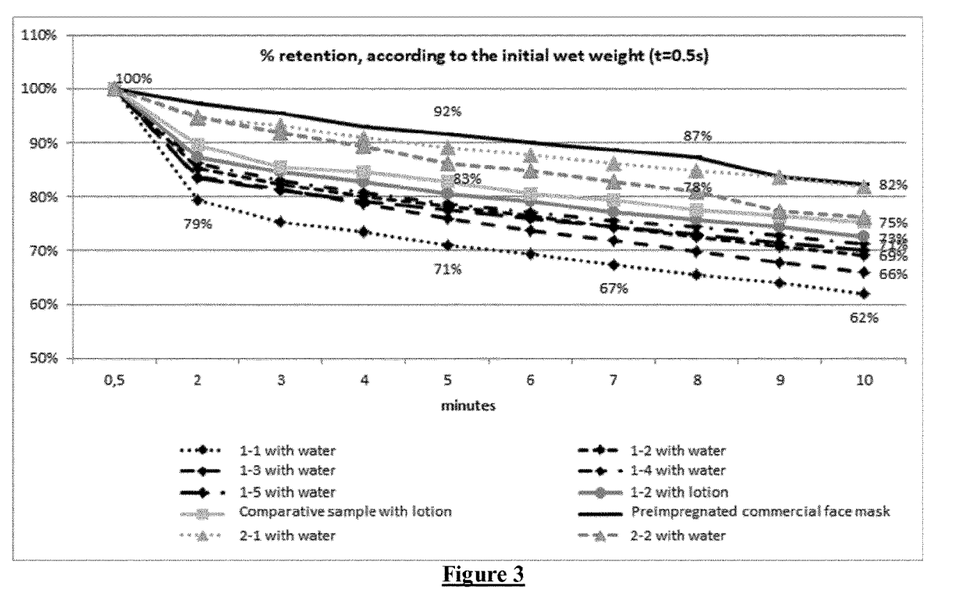

FIG. 3 illustrates the release capacity (or retention) for the eight different vegetable papers of Examples 1-1 to 2-2 with water, for the vegetable paper of Example 1-2 with the Technature lotion, for a preimpregnated commercial face mask and for a commercial face mask made of synthetic fibres with the Technature lotion (referred as comparative sample with lotion in FIG. 3).

The various exemplified vegetable papers have absorption capacities inferior to that of the commercial mask, but have equivalent release capacities. This may be advantageous for the face mask manufacturer, since a face mask, the substrate of which is an exemplified vegetable paper, consumes less cosmetic lotion than the commercial mask made of synthetic fibres and releases it just as well as the commercial mask made of synthetic fibres. By virtue of the vegetable paper according to the invention, the face mask manufacturer can make savings on the amount of lotion required per mask.

Example 3-4: Evaluation of the Dry and Wet Strengths

Figure 4:
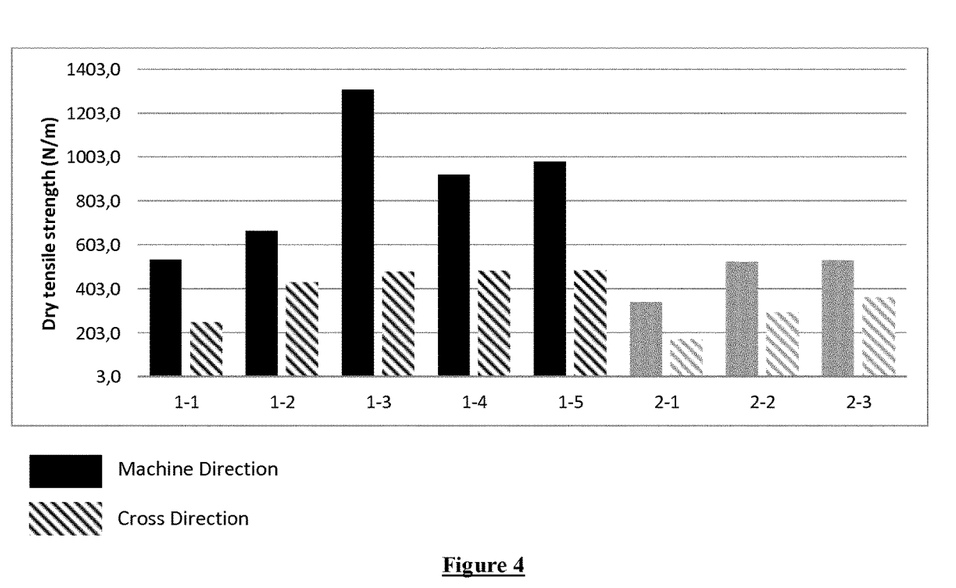

FIG. 4 illustrates the dry tensile strengths in the Machine Direction (MD) and in the Cross Direction (CD) for the eight exemplified vegetable papers with water.

All the exemplified vegetable papers have entirely satisfactory dry strengths for use in the manufacture of face masks.

Figure 5:
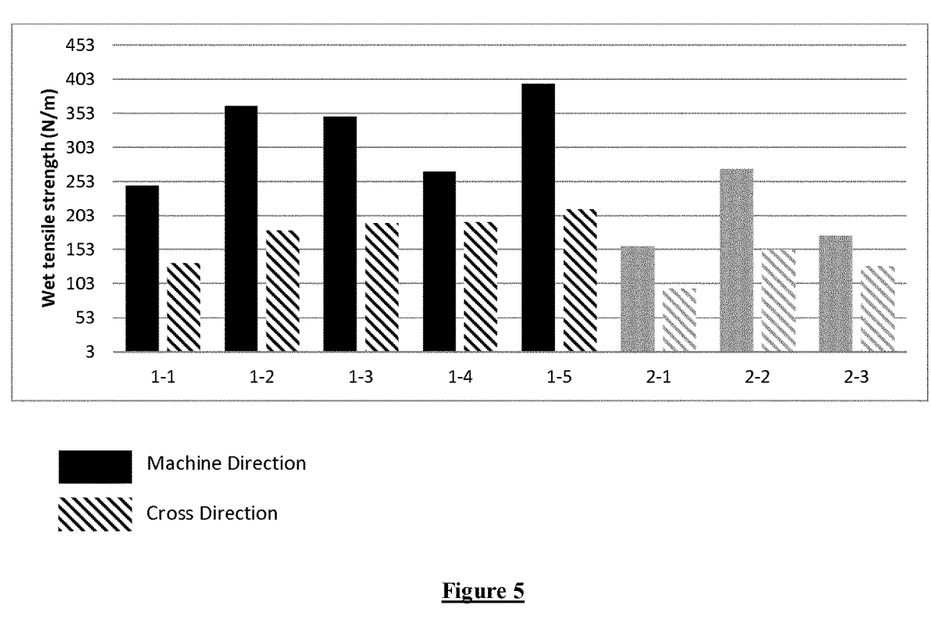

FIG. 5 illustrates the wet tensile strengths in the Machine Direction (MD) and in the Cross Direction (CD) for the eight exemplified vegetable papers with water.

All the exemplified vegetable papers have entirely satisfactory wet strengths for use as substrate for cosmetic face masks.

Example 4: Treatment by Hydroentanglement of the Vegetable Papers of Example 1

Example 4-1: Treatment Process

Each of the vegetable papers of Example 1 is subjected to a hydroentanglement treatment with three increasing levels of total pressure:
- level 1: 2 injectors: 30+40=70 bar,
- level 2: 2 injectors: 47+67=114 bar
- level 3: 2 injectors: 62+88=150 bar.

The injectors have a diameter of 110 µm and are 1 mm apart.

Example 4-2: Properties of the Vegetable Papers which have Undergone the Treatment The hydroentanglement reduces the dry and wet strength of the vegetable papers of Example 1. However, the deformability of the papers is greatly improved by this treatment.

The sensory properties of the vegetable paper of Example 1-2 after hydroentanglement treatment were evaluated by a cosmetic panel.

Relative to the untreated vegetable paper, the softness of the treated vegetable paper, its drape and its conformability are increased; in particular, its conformability is comparable to that of a commercial product. Furthermore, the marking of the folds has reduced. The treated vegetable paper also absorbs more water and dries less quickly than the untreated vegetable paper.

The vegetable paper of Example 1-2 after hydroentanglement treatment may thus advantageously replace substrates for commercial face masks based on synthetic fibres.

The invention claimed is:

1. A vegetable paper comprising a mixture of bast fibres and cellulose fibres, wherein
   the amount of bast fibres is at least 40% by weight of dry matter of the vegetable paper,
   the amount of cellulose fibres is at least 10% by weight of dry matter of the vegetable paper, and
   the bast fibres have a length-weighted average length of from 1 mm to 12 mm, the mixture of bast fibres and cellulose fibres has a degree of refinement from 5° SR to 50° SR, wherein ° SR stands for Schopper-Riegler, and wherein the basis weight of the vegetable paper is from 15 g/m² to 70 g/m².

2. The vegetable paper according to claim 1, wherein the bast fibres are selected from hemp fibre, Indian hemp fibre, jute fibre, kenaf fibre, kudzu fibre, *Dalbergia ecastaphyllum* fibre, flax fibre, okra fibre, nettle fibre, papyrus fibre, ramie fibre, sisal fibre, esparto fibre, and mixtures thereof.

3. The vegetable paper according to claim 1, wherein the bast fibres have undergone extraction in a solvent.

4. The vegetable paper according to claim 1, wherein the cellulose fibres are selected from wood pulp, lyocell fibres, viscose fibres, cellulose acetate fibres, and mixtures thereof.

5. The vegetable paper according to claim 4, wherein the amount of lyocell fibres is from 10% to 40% by weight of dry matter of the vegetable paper.

6. The vegetable paper according to claim 4, wherein the amount of wood pulp is from 10% to 40% by weight of dry matter of the vegetable paper.

7. The vegetable paper according to claim 1 further comprising an additive selected from a wet strength agent, a dry strength agent, a softening agent, a lotion composition, a wetting agent, latex, a cannabinoid, and mixtures thereof.

8. The vegetable paper according to claim 7 wherein the additive is a cannabinoid.

9. The vegetable paper according to claim 7, wherein the amount of additive is less than 3% by weight of dry matter of the vegetable paper.

10. A hybrid paper comprising the vegetable paper as defined in claim 1 and a second paper, said second paper being a spunbound support or being manufactured via a wet laid process, a drylaid carded process using long artificial fibres, long natural fibres, cellulose fibres, and mixtures thereof, or an airlaid process using long artificial fibres, long natural fibres, cellulose fibres, and mixtures thereof.

11. A cosmetic product comprising the vegetable paper as defined in claim 1.

12. The cosmetic product according to claim 11 wherein the cosmetic product is a cosmetic mask, an eye patch, a body envelope, or a wipe.

13. The cosmetic product according to claim 11 further comprising an active principle chosen from sebum regulators, antimicrobial agents, antibacterial agents, matt-effect agents, astringents, acidifying agents, cicatrizing agents, exfoliants or kerato-regulating agents, occlusive agents, protective agents, disinfectants, emollients, nourishing agents, moisturizers, anti-ageing agents, calmatives, decongestants or veinotonic agents, occlusive agents, UV-screening agents, humectants, hygroscopic agents, gelling agents, exfoliants, anti-free radical, cell-regenerating or cell-stimulating agents, firming agents, tautening agents, anti-glycation agents, lightening agents, and mixtures thereof.

14. A wipe comprising the vegetable paper as defined in claim 1.

15. A hygiene paper comprising the vegetable paper as defined in claim 1.

16. An absorbent paper comprising the vegetable paper as defined in claim 1.

17. A process for manufacturing a vegetable paper as defined in claim 1 via a wet route.

18. The process according to claim 17 comprising the following steps:
   a) mixing bast fibres with a solvent to extract all or some of the bast fibre compounds that are soluble in the solvent,
   b) separating of the bast fibres from the soluble compounds to obtain the bast fibres which have undergone extraction in a solvent,
   c) forming the vegetable paper via a wet process using the bast fibres which have undergone extraction in a solvent.

19. Process according to claim 17, wherein the vegetable paper undergoes an additional hydroentanglement treatment.

20. The vegetable paper according to claim 1, wherein the amount of cellulose fibres is at least 20% by weight of dry matter of the vegetable paper.

* * * * *